United States Patent
Alzoman

(10) Patent No.: US 10,729,426 B1
(45) Date of Patent: Aug. 4, 2020

(54) SUTURE NEEDLE RETAINING STRAP

(71) Applicant: KING SAUD UNIVERSITY, Riyadh (SA)

(72) Inventor: Hamad Abdulrahman Alzoman, Riyadh (SA)

(73) Assignee: King Saud University, Riyadh (SA)

( * ) Notice: Subject to any disclaimer, the term of this patent is extended or adjusted under 35 U.S.C. 154(b) by 0 days.

(21) Appl. No.: 16/586,484

(22) Filed: Sep. 27, 2019

(51) Int. Cl.
*A61B 17/04* (2006.01)
*A61B 17/00* (2006.01)
*A45F 5/00* (2006.01)

(52) U.S. Cl.
CPC ...... *A61B 17/0483* (2013.01); *A61B 17/0482* (2013.01); *A45F 2005/006* (2013.01); *A61B 2017/00424* (2013.01)

(58) Field of Classification Search
CPC ......... A45F 2005/006; A45F 2005/008; A61B 2017/00424; A61B 2050/21; Y10T 24/13; Y10T 24/1382; Y10T 24/1397
See application file for complete search history.

(56) References Cited

U.S. PATENT DOCUMENTS

| | | | |
|---|---|---|---|
| 2,176,052 A | 10/1939 | Beyer | |
| 2,449,882 A * | 9/1948 | Daniels | A61M 25/02 604/179 |
| 5,353,974 A | 10/1994 | Maurizio | |
| 5,617,952 A | 4/1997 | Kranendonk | |
| 8,517,233 B2 | 8/2013 | Podda-Heuback | |
| 10,098,632 B2 | 10/2018 | Gorek et al. | |
| 2016/0089204 A1* | 3/2016 | Chow | A61B 50/20 224/217 |

FOREIGN PATENT DOCUMENTS

GB      2413056 A      10/2005

OTHER PUBLICATIONS

"YEQIN NEW Magnetic Wrist Pin Holder," 1996-2019, Amazon.com, Inc.

* cited by examiner

*Primary Examiner* — Robert Sandy
(74) *Attorney, Agent, or Firm* — Richard C. Litman; Nath, Goldberg & Meyer

(57) ABSTRACT

The present subject matter provides a magnetic suture needle retaining strap to be worn by a surgeon during a surgery. The strap includes a band and a housing on an outer surface of the band. The housing includes an inner chamber, an opening leading into the chamber, and a magnet. The band may be placed around a palm of the surgeon's non-dominant hand. The housing provides a dock for retaining the suture needle while the surgeon is knotting the suture or performing other tasks that require use of both hands.

12 Claims, 4 Drawing Sheets

US 10,729,426 B1

SUTURE NEEDLE RETAINING STRAP

BACKGROUND

1. Field

The disclosure of the present patent application relates to surgical suturing, and particularly to a device worn on a practitioner's hand that safely secures the suture needle while the practitioner knots or performs other tasks.

2. Description of the Related Art

Many common medical procedures, including oral surgery, involve closing tissue by the use of sutures. A suture is a thread or fiber which can be used to close previously opened tissue. The suture needle is a needle-like instrument with a sharp point at one end and an opening at an opposing end for threading. Suture needles vary in size and shape, and the choice of a particular size or shape of suture needle is dictated by the type of medical procedure to be performed. One common form of suture needle has an arcuate configuration. A wound or surgical incision can be stitched together using a suture needle and suture, in much the same manner that two pieces of cloth are sewn together with a threaded needle.

The suture and suture needle must be sterile to minimize the risk of infection to the patient. Many common medical procedures require the surgeon to use a number of different tools. In these circumstances, the surgeon must be careful to keep the suture needle in a sterile area as it is exchanged for another tool. Further, the suture needle, as well as other tools, must be readily at hand for the surgeon's use during the operation. This is not simply a matter of convenience, as the patient's safety may depend on a specific tool being quickly available if it should be needed. Therefore, the suture needle (and other instruments) must be placed on a convenient sterile surface during an operation so that they may be readily accessed by the surgeon, while maintaining the sterility of the operating area.

It is also important to minimize the risk of self-contamination for a surgeon using a suture needle. A surgeon who works with gloved hands, for example, may struggle to pick up the needle from a flat surface due to interference from the gloves. This struggle can increase the likelihood of an accidental prick, especially if the surgeon must put down and pick up a suture needle (with a suture attached) several times during the course of an operation. Furthermore, the surgeon typically holds the needle between thumb and index fingers to protect the patient while tying the suture. This strategy may protect the patient but increases the likelihood of injuring the surgeon's hand.

Thus, a suture needle retaining strap solving the aforementioned problems is desired.

SUMMARY

The present subject matter provides a magnetic suture needle retaining strap to be worn by a surgeon during a surgery. The strap includes a band and a housing on an outer surface of the band. The housing includes an inner chamber, an opening leading into the inner chamber, and a magnet. The band may be placed around a palm of the surgeon's non-dominant hand. The housing provides a dock for retaining the suture needle while the surgeon is knotting the suture or performing other task that requires use of both hands.

These and other features of the present disclosure will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

The present subject matter provides a suture needle retaining strap to be worn by a surgeon during a surgery. The strap may be placed around a palm of the surgeon's non-dominant hand to hold the suture needle while the surgeon is knotting the suture or performing other tasks that require use of both hands. The strap includes a band and a housing with an inner chamber. A magnet is provided within or adjacent to the inner chamber. Instead of holding the suture needle between two fingers or letting the needle dangle while performing tasks, the surgeon may insert the tip of the needle into the inner chamber of the housing to be held by the magnet. The housing can provide a sterile space to store the needle while protecting the surgeon's hand from the needle tip.

Figure 1:
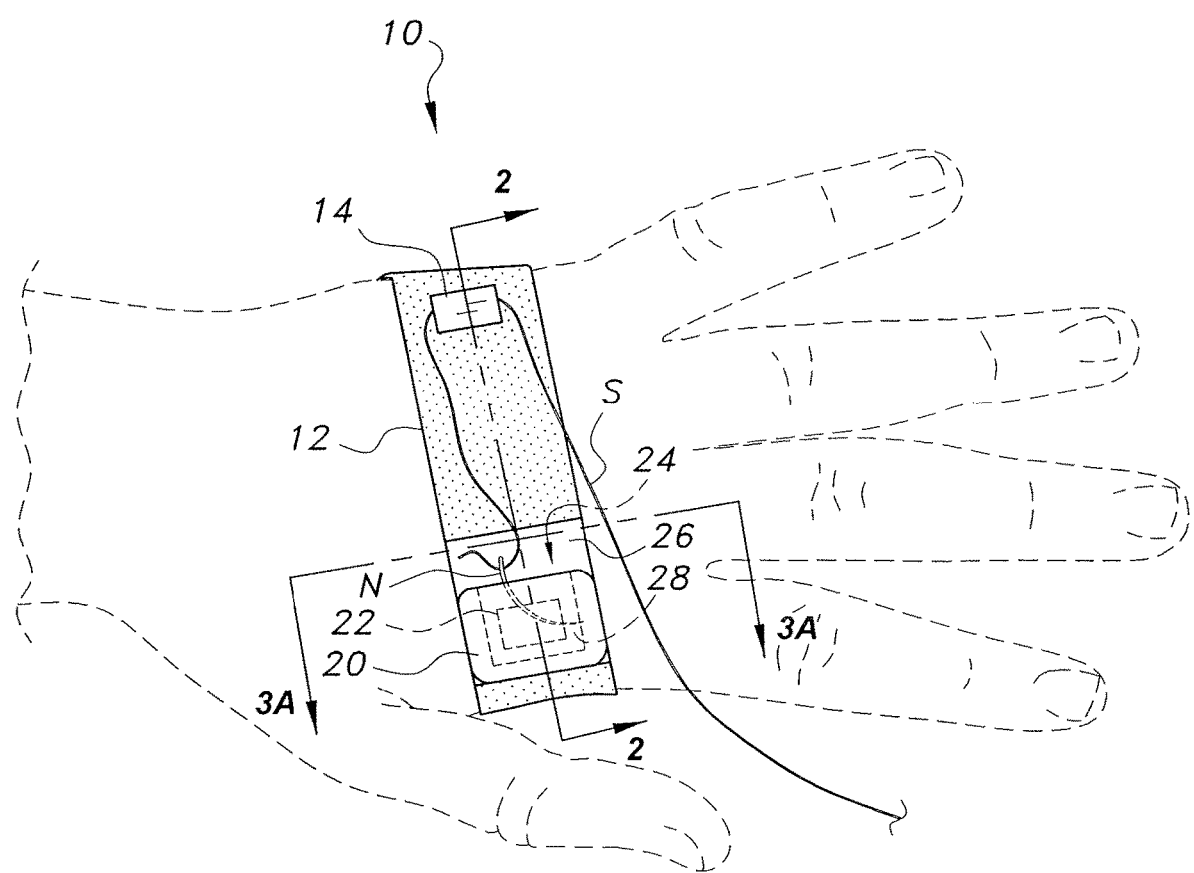
FIG. 1 is a perspective view of a suture needle retaining strap being worn on a hand of a user.

FIG. 1 shows an embodiment of the suture retaining strap 10. The strap 10 includes a band 12 that is configured to be wrapped around the hand of a user and a housing 20 on an outer surface of the band 12. The band 12 may be made of an elastic material to accommodate various hand sizes. Alternatively, the band 12 may be formed from other suitable material and may include a suitable fastening material that allows for size adjustment, such as a buckle or a hook-and-loop fastening material. The housing 20 includes an inner chamber 28, an opening 24 leading into the chamber 28, and a magnet 22. A suture needle N can be removably positioned in the inner chamber 28 and the magnet 22 can facilitate retaining the suture needle N within the chamber 28 until needed.

In an embodiment, the strap 10 can include a puncture resistant sheet 26 on an outer surface of the band 12 to protect the user's hand while the needle N is being placed into the opening 24 of the housing 20.

In an embodiment, the strap 10 may include an upright hook or post 14 on an outer surface of the band 12 to hold the suture S while the needle N is in the housing 20. The post 14 may be spaced from the housing 20. The post 14 may include a notch for receiving and stabilizing a portion of the suture S. Once the needle N is inserted into the housing 20, the attached suture S may be held by the notched post 14.

Figure 2:
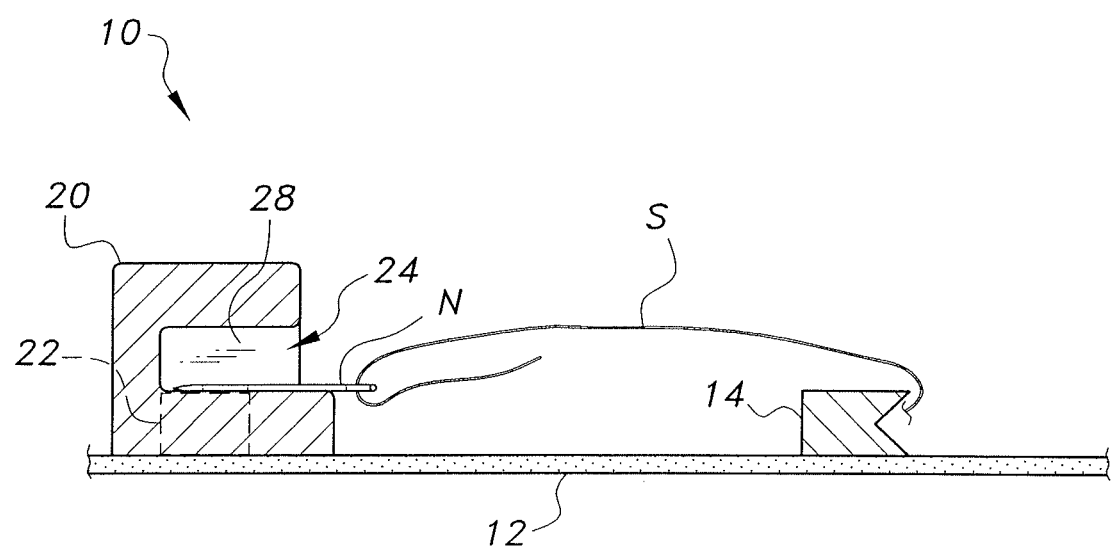
FIG. 2 is a section view drawn along lines 2-2 of FIG. 1.

FIG. 2 shows a cross-section of the suture needle retaining strap 10 along lines 2-2 of FIG. 1. The magnet 22 can be on or within a wall of the housing 20 to provide a support surface upon which the needle N may be placed. The magnet 22 may be any type of static magnet known in the art, such as neodymium iron boron, samarium cobalt, alnico, ceramic, and ferrite. The magnet 22 may have any suitable shape and/or size. In some non-limiting embodiments, at least a portion of the magnet 22 and/or the inner chamber 28 may be coated with a soft material, such as a polymer-like silicone, which will not dull the needle N point upon contact. In some non-limiting embodiments, the housing 20 may be made of a soft material, such as silicon or rubber, to prevent dulling the needle N upon contact.

When the needle N is inserted into the chamber 28 of the housing 20, the magnet 22 can hold the needle N within the inner chamber 28 such that the needle N point is fully surrounded by the housing 20. The inner chamber 28 may be sized so that the end of the needle N that is attached to the suture S extends out of the chamber 28 to allow the user to easily grab and adjust the needle N. When the needle N is held in the housing 20, the suture S can be wrapped around the post or held by the surgeon (see FIG. 4), depending on the task.

Figure 3A:
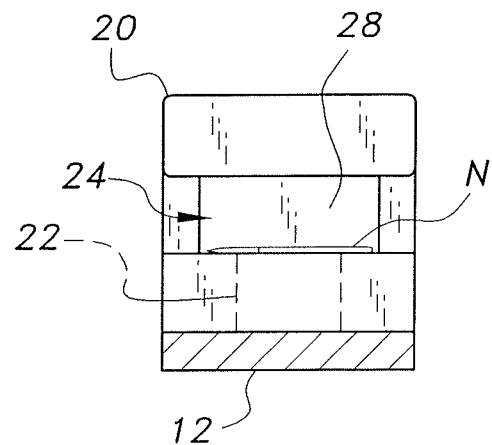
FIG. 3A is a section view drawn along lines 3A-3A of FIG. 1.
Figure 3B:
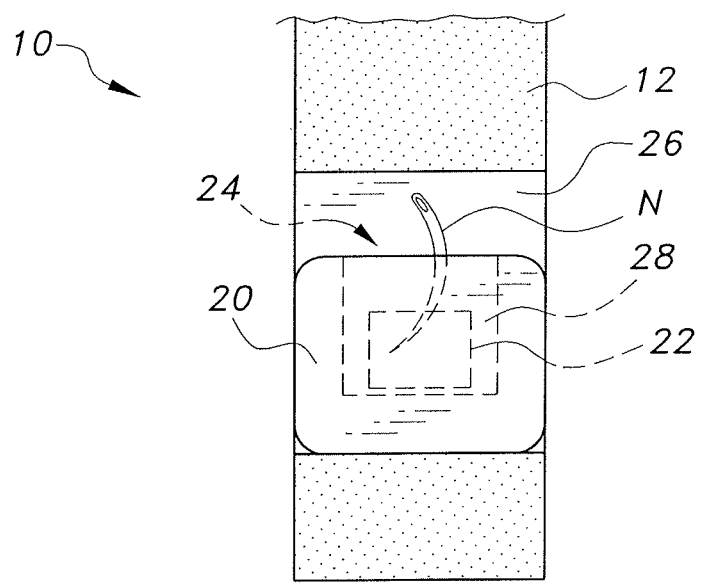
FIG. 3B is an overhead view of the suture needle retaining strap of FIG. 1 detailing the housing.

FIG. 3A shows a side view of the housing 20 from the end of the housing that includes the opening 24. The housing 20 includes side walls and an end wall to fully surround the needle N point within the inner chamber 28. FIG. 3B shows a top view of the housing 20. A puncture resistant sheet 26 may be provided on an upper surface of the band 12 proximate the opening 24 of the housing 20. The sheet 26 protects the user from unintended pricks by the needle N during insertion of the needle N into the opening 24 of the housing 20. The inner chamber 28 of the housing 20 may be sized based on the size of the needle N. In some cases, the inner chamber 28 may have a depth ranging from about 50 to 90 percent of the needle N length. A size of the magnet 22 may be determined based on the amount of magnetic force desired by the user.

Figure 4:
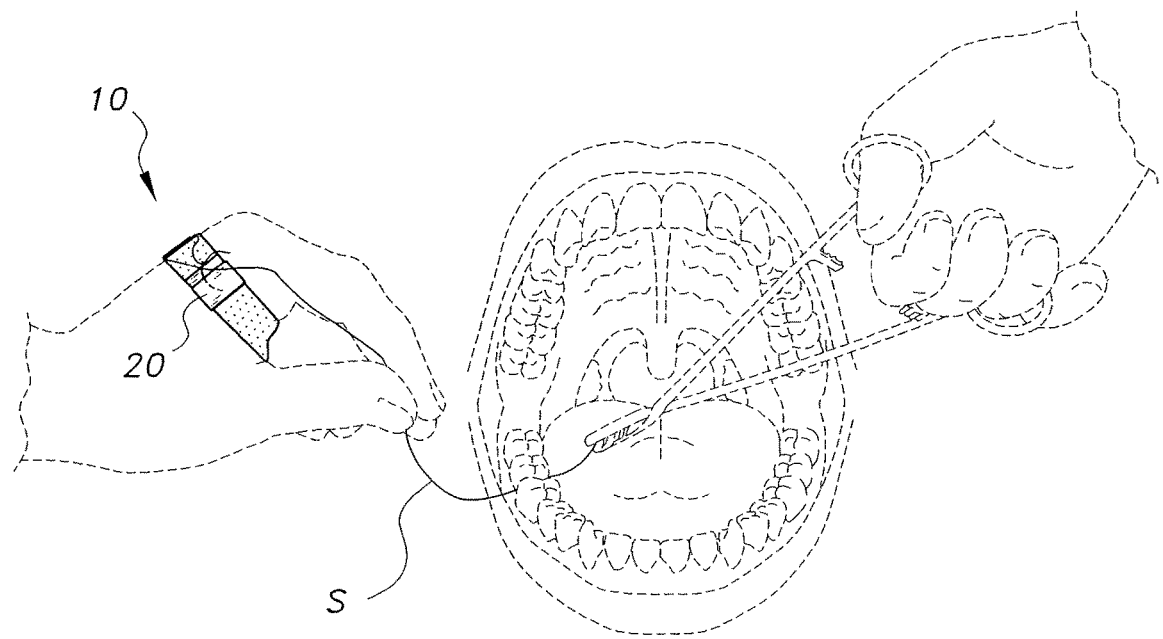
FIG. 4 is an environmental perspective view of the suture needle retaining strap being worn by a user during a procedure.

FIG. 4 shows the suture needle retaining band 10 in use during an oral surgical procedure. The surgeon is in the process of knotting the suture S while the needle N is in the housing 20. The housing 20 prevents the needle N point from contacting the surgeon, the patient, and any medical equipment. As such, the strap 12 safely retains the needle and allows the surgeon to have full use of both hands to knot the suture S.

It is to be understood that the present subject matter is not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

I claim:

1. A suture needle retaining strap, comprising:
   a band configured to be wrapped around a palm of a user;
   a housing attached to an outer surface of the band, the housing including an inner chamber, an open end leading into the inner chamber, and a magnet; and
   an upright post attached to the outer surface of the band, a first surface of the post facing the housing and a second, opposing surface of the post faced away from the housing.

2. The suture needle retaining strap of claim 1, further comprising a puncture resistant sheet attached to the outer surface of the band adjacent the housing on a side of the opening.

3. The suture needle retaining strap of claim 1, wherein the band is elastic.

4. The suture needle retaining strap of claim 1, wherein a circumference of the band is adjustable.

5. The suture needle retaining strap of claim 1, wherein the post further comprises a notch defined within the opposing, second surface of post.

6. The suture needle retaining strap of claim 1, wherein the magnet is disposed within a wall of the housing.

7. The suture needle retaining strap of claim 1, wherein the magnet includes at least one material selected from the group consisting of neodymium iron boron, samarium cobalt, alnico, ceramic, and ferrite.

8. A suture needle retaining strap, comprising:
   a band configured to be wrapped around a palm of a user;
   a housing attached to an outer surface of the band, the housing including an inner chamber, an open end leading into the inner chamber, and a magnet; and
   an upright post attached to the outer surface of the band, the upright post including a first surface facing the housing, a second, opposing surface facing away from the housing, and a notch defined within the second surface.

9. The suture needle retaining strap of claim 8, further comprising a puncture resistant sheet attached to the outer surface of the band adjacent the housing proximate the opening.

10. The suture needle retaining strap of claim 8, wherein the band is elastic.

11. The suture needle retaining strap of claim 8, wherein a circumference of the band is adjustable.

12. The suture needle retaining strap of claim 8, wherein the magnet is disposed within a wall of the housing.

* * * * *